United States Patent [19]

Leistner et al.

[11] 4,371,651
[45] Feb. 1, 1983

[54] STABILIZER COMPOSITIONS AND POLYVINYL HALIDE RESIN COMPOSITIONS CONTAINING 1,3-DICARBONYL COMPOUNDS

[75] Inventors: William E. Leistner, Atlantic Beach, N.Y.; Motonobu Minagawa, Kosigaya, Japan; Kouji Tsuruga, Omiya, Japan; Masashi Harada, Yokohama, Japan

[73] Assignee: Phoenix Chemical Corporation, Atlantic Beach, N.Y.

[21] Appl. No.: 226,582

[22] Filed: Jan. 21, 1981

[30] Foreign Application Priority Data

Aug. 14, 1980 [JP] Japan ................. 55-112303

[51] Int. Cl.³ ................. C08K 5/07; C09K 15/06
[52] U.S. Cl. ................. 524/178; 252/400 R; 252/405; 252/407; 524/109; 524/147; 524/204; 524/236; 524/237; 524/323; 524/327; 524/357; 524/394
[58] Field of Search ........... 260/45.7 R, 45.75 W, 260/45.9 R, 429 J; 568/331, 335, 412; 252/400 R, 407; 524/178, 357, 237

[56] References Cited

U.S. PATENT DOCUMENTS

| | | |
|---|---|---|
| 2,659,711 | 11/1953 | Wilkins et al. ........... 568/335 |
| 2,922,738 | 1/1960 | McDermott et al. ........... 260/429 J |
| 3,458,548 | 7/1969 | Carlson ........... 568/331 |
| 3,492,267 | 1/1970 | Wood ........... 524/357 |
| 4,102,839 | 7/1978 | Crochemore et al. ........... 524/357 |
| 4,116,907 | 9/1978 | Shiohara et al. ........... 524/357 |
| 4,123,400 | 10/1978 | Gay ........... 260/45.95 L |
| 4,217,258 | 8/1980 | Minagawa et al. ........... 524/178 |
| 4,221,687 | 9/1980 | Minagawa et al. ........... 260/45.75 W |
| 4,282,141 | 8/1981 | Minagawa et al. ........... 524/357 |

OTHER PUBLICATIONS

Martin et al., J.A.C.S., vol. 80, pp. 4891-4895, 1958.

Primary Examiner—John Kight, III
Assistant Examiner—R. A. White

[57] ABSTRACT

Stabilizer compositions and polyvinyl halide resin compositions containing 1,3-dicarbonyl compounds having the formula:

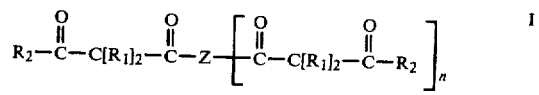

as well as metal and organotin enolate salts thereof, effective in enhancing the resistance to deterioration by heat and light of polyvinyl halide resins.

6 Claims, No Drawings

STABILIZER COMPOSITIONS AND POLYVINYL HALIDE RESIN COMPOSITIONS CONTAINING 1,3-DICARBONYL COMPOUNDS 1,3-Dicarbonyl compounds are known stabilizers for halogen-containing resins.

J. Darby, U.S. Pat. No. 2,669,548, patented Feb. 16, 1954, discloses halogen-containing resin compositions having improved stability containing a mixture of a zinc salt and a calcium chelate derivative of a 1,3-dicarbonylic compound.

F. Ebel, U.S. Pat. No. 3,001,970, patented Sept. 26, 1961, discloses preventing the discoloration of vinylidene chloride polymers by light by adding a small amount of dibenzoyl methane.

British Pat. No. 1,141,971 of May 23, 1967 to W. R. Grace & Co. discloses zinc complexes of beta-dicarbonyl compounds, used as stabilizing additives for chlorine-containing polymers.

L. Weisfeld, U.S. Pat. No. 3,493,536, patented Feb. 3, 1970, discloses that diaroylmethane compounds provide stabilizing action against the sensitizing effect of bismuth or antimony compounds on chlorine-containing materials.

M. Crochemore, U.S. Pat. No. 4,102,839, patented July 25, 1978, discloses the possibility of preventing the thermal breakdown of vinyl chloride polymers by adding one or more metal salts and a 1,3-dicarbonyl compound.

M. Gay, U.S. Pat. Nos. 4,123,399 and 4,123,400, patented Oct. 31, 1978, discloses vinyl chloride compositions containing metal salts, polyol and a 1,3-dicarbonyl compound.

1,3-Dicarbonyl compounds are known that contain carboxy or ester groups, but not as vinyl chloride polymer stabilizers. 1,3-Dicarbonyl compounds containing carboxy or ester groups can be prepared by the base-catalyzed condensation reaction of a diester of benzene dicarboxylic acid with a ketone (see, for example, B. T. Brown et al, *Pestic. Sci.* 1973, 473–484) or by reaction of a carboxy acetophenone with a carboxylic ester (see, for example, H. Imai et al, *Nippon Kagaku Kaishi* 1977 1081).

In accordance with the present invention, 1,3-dicarbonyl compounds are provided having the formula:

$$R_2-\overset{O}{\underset{\|}{C}}-C[R_1]_2-\overset{O}{\underset{\|}{C}}-Z\left[-\overset{O}{\underset{\|}{C}}-C[R_1]_2-\overset{O}{\underset{\|}{C}}-R_2\right]_n \quad \text{I}$$

wherein:

$R_1$ is selected from the group consisting of hydrogen, hydrocarbon groups having from one to about eighteen carbon atoms and such groups substituted with one or more groups selected from the group consisting of halogen, hydroxy, alkoxy $OR_1$, ester $COOR_1$, alkyl and alkoxycarbonyl alkyl having from one to about eighteen carbon atoms, and

$R_2$ is selected from the group consisting of hydrocarbon having from one to about eighteen carbon atoms and such groups substituted with one or more groups selected from the group consisting of halogen, hydroxy, alkoxy $OR_1$, ester $COOR_1$, alkyl and alkoxycarbonyl alkyl having from one to about eighteen carbon atoms;

one $R_1$ and $R_2$ may be linked together as an alkylene group to form a cyclic or ring structure;

n is a number from 1 to 3; and

Z is a polyvalent linking radical selected from the group consisting of a direct linkage between the

polyvalent hydrocarbon $R_3$;

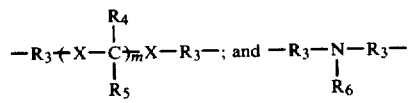

wherein:

$R_3$ is polyvalent hydrocarbon group having from one to about eighteen carbon atoms;

$R_4$ and $R_5$ are selected from the group consisting of hydrogen and hydrocarbon groups having from one to about eighteen carbon atoms; and $R_4$ and $R_5$ may be linked together as an alkylene to form a cyclic or ring structure;

X is —O— or —S—;

m is 0 or 1; and $R_6$ is selected from the group consisting of hydrogen, hydrocarbon having from one to about eighteen carbon atoms, and —$R_3$—; as well as metal and organotin enolate salts thereof.

The compounds are effective in enhancing the resistance to deterioration by heat and light of polyvinyl halide resins.

The 1,3-dicarbonyl compound is employed with such resins in an amount within the range from 0.0001 to 3 parts, preferably from 0.001 to 1 part, by weight of the resin.

These compounds also exist in the equilibrium forms of metal and organotin enolate salts of one or more (in admixture) of the various enol forms exemplified by the species:

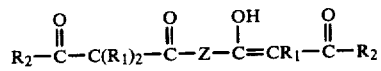

(assuming one $R_1$ = H)

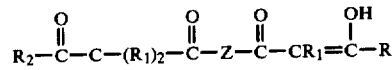

The metal as in other enolate salts replaces one or more hydrogens of the enol hydroxyl, according to the valence of the metal, producing various enolate salts exemplified by the forms:

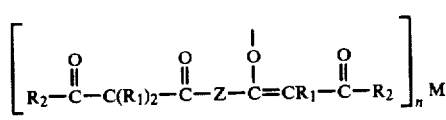

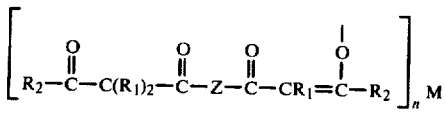

which salts are accordingly represented generically herein by the formula:

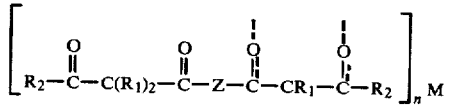

it being understood that one hydrogen is replaced by M at one enol group.

n represents the valence of M. M is any metal, monovalent or polyvalent, preferably a metal conventionally used in metal salt stabilizers for polyvinyl chloride resins, such as lithium, sodium, potassium, magnesium, strontium, barium, calcium, cadmium, lead, zinc, aluminum, antimony, tin or zirconium, as well as organotin $(R)_mSn$ where m is one, two or three, and R is a hydrocarbon group having from one to about eighteen carbon atoms.

The tautomeric equilibrium between form I and forms II and III can be represented as follows:

For the monovalent metal salts M, the equilibrium becomes:

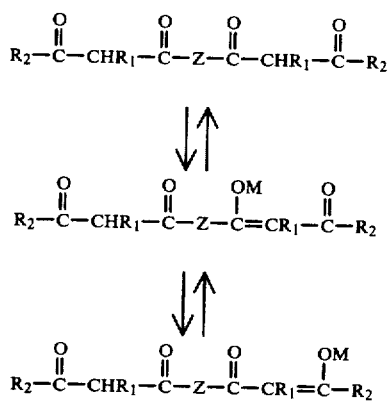

For polyvalent metal salts, the 1,3-dicarbonyl radical is multiplied according to the valence of M.

All forms of 1,3-dicarbonyl compounds of this invention are effective in stabilizing polyvinyl halide resins. When M is a metal, while numerous structural formulae can be written, differing in the location of metal in the enolate, all are equivalent, and therefore the formula is better represented as a hybrid of all formulae than any single one.

The M organotin group has from one to three hydrocarbon groups R linked to tin through carbon. Each hydrocarbon group R linked to carbon can have from one to eighteen carbon atoms. The hydrocarbon groups R include alkyl, cycloalkyl, aryl, and alkylaryl groups. The R group can also be substituted with one or more ester groups $COOR_2$. Alkyl groups and alkoxycarbonyl alkyl groups are preferred.

Exemplary R groups include methyl, butyl, hexyl, octyl, isooctyl, 2-ethyl hexyl, nonyl, decyl, stearyl; cyclohexyl, cyclopentyl, cycloheptyl; phenyl, benzyl, phenethyl, naphthyl; methoxycarbonylethyl, ethoxycarbonylmethyl, and butoxycarbonylethyl.

The total of the number of organic groups R linked to tin through carbon plus the number of 1,3-dicarbonyl groups is:

| Type of organotin group: | Monoorganotin $RSn$ | Diorganotin $R_2Sn$ | Triorganotin $R_3Sn$ |
| --- | --- | --- | --- |
| Number of 1,3 dicarbonyl groups: | 3 | 2 | 1 |

The organic groups R linked to tin through carbon can be the same or different.

Representative organotin groups include monomethyltin, mono-n-butyltin, monoisobutyltin, mono-2-ethylhexyltin, methoxycarbonylethyltin; dimethyltin, di-n-butyltin, di(ethoxycarbonylethyl)tin, methyl-n-octyltin, n-butyl-n-butoxycarbonylethyltin, di-n-octyltin; tri(methoxycarbonylethyl)tin, tri-n-octyltin, and methyl di(2-ethylhexyloxycarbonylethyl)tin.

The hydrocarbon groups $R_1$, $R_2$ and $R_3$ can be open chain or cyclic, and include such aliphatic, cycloaliphatic and aromatic hydrocarbon groups as alkyl groups having from one to about eighteen carbon atoms; cycloalkyl, cycloalkylalkylene, and alkylcycloalkyl groups having from five to about eighteen carbon atoms; and aryl groups (including aralkyl and alkaryl groups) having from six to about eighteen carbon atoms; for example, methyl, ethyl, propyl, isopropyl, butyl, isobutyl, sec-butyl, tert-butyl, amyl, tert-amyl, tert-hexyl, tert-heptyl, iso-heptyl, tert-octyl, 2,4,4-trimethylpentyl, 2-ethylhexyl, iso-octyl, nonyl, decyl, dodecyl, tridecyl, tetradecyl, pentadecyl, hexadecyl, heptadecyl, octadecyl; 1-methylcyclopentyl, cyclohexyl, cycloheptyl; phenyl, naphthyl, methylphenyl, ethylphenyl, butylphenyl, t-butylphenyl, octylphenyl, nonylphenyl, dimethylphenyl, benzyl and phenethyl.

Substituted hydrocarbon $R_1$, $R_2$ and $R_3$ groups include trifluoromethyl, trichloromethyl, hydroheptadecyl, methoxyethyl, hydroxyphenyl, methoxyphenyl, methylenedioxyphenyl, carbomethoxyphenyl and chlorophenyl.

Particularly preferred 1,3-dicarbonyl compounds represented by the above general formulae according to the invention include the compounds shown below, as well as their enol tautomers, and metal enolates and organotin enolates:

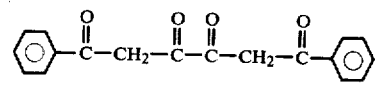

1.

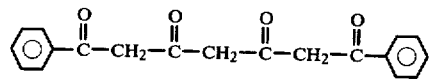

2.

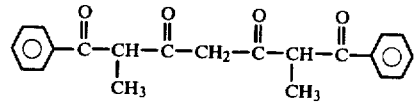

3.

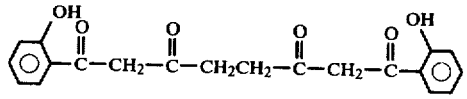

4.

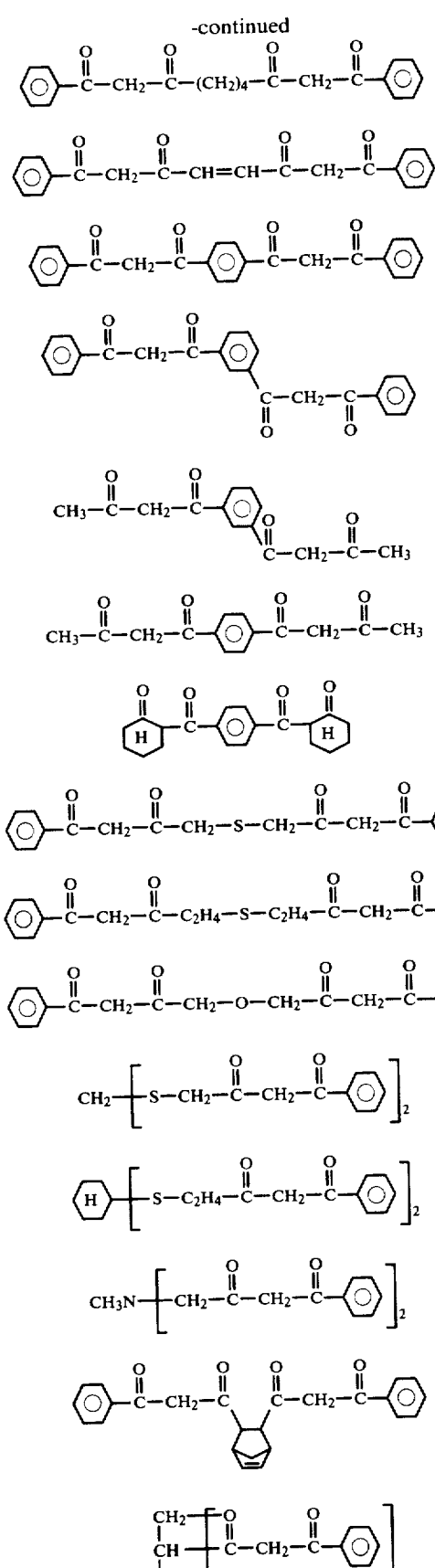
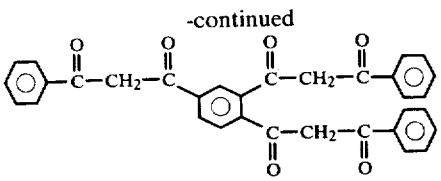
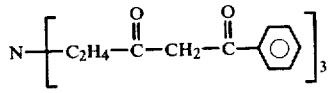
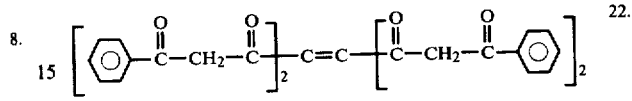

These compounds can be named as follows:

1. 1,4-Dibenzoylbutane-2,3-dione
2. 1,5-Dibenzoylpentane-2,4-dione
3. 2,7-Dibenzoyloctane-3,6-dione
4. 1,8-Bis(2-hydroxybenzoyl)octane-2,7-dione
5. 1,12-Dibenzoyldodecane-2,11-dione
6. 1,6-Dibenzoyl-3-hexene-2,5-dione
7. 1,4-Bis(benzoylacetyl)benzene
8. 1,3-Bis(benzoylacetyl)benzene
9. 1,3-Bis(acetoacetyl)benzene
10. 1,4-Bis(acetoacetyl)benzene
11. 1,4-Bis(2-ketocyclohexanoyl)benzene
12. 1,7-Dibenzoyl-4-thiaheptane-2,6-dione
13. 1,9-Dibenzoyl-5-thianonane-2,8-dione
14. 1,7-Dibenzoyl-4-oxaheptane-2,6-dione
15. 1,9-Dibenzoyl-4-6-dithianonane-2,8-dione
16. 1,1-Bis(benzoylacetylethylthio)cyclohexane
17. N,N-Bis(benzoylacetylmethyl)methylamine
18. 2,3-Bis(benzoylacetyl)bicyclo(2,2,1)heptene-5
19. 1,2,3-Tris(benzoylacetyl)butane
20. 1,2,4-Tris(benzoylacetyl)benzene
21. N,N,N-Tris(benzoylacetylethyl)amine
22. 1,1,2,2-Tetrakis(benzoylacetyl)ethylene The 1,3-dicarbonyl compounds are prepared by the conventional procedures described in the prior art referred to above.

The preparation of the 1,3-dicarbonyl compounds is illustrated by the following Examples:

EXAMPLE I

Preparation of 1,4-dibenzoylbutane-2,3-dione

A mixture of 11.8 g of dimethyloxalate, 15.6 g of sodiumamide and 300 ml of diethyl ether was cooled, and 36 g of acetophenone was added dropwise at 0° to 5° C. After addition was completed, the whole was stirred at 0° to 5° C. for two hours, and held an additional two hours at room temperature. Water was added in a reactor, and the water layer was separated and neutralized. The resulting precipitate was recrystallized from acetone. The product was a white powder, melting point 178° to 180° C.

EXAMPLE II

Preparation of 1,12-dibenzoyldodecane-2,11-dione

A mixture of 11.8 g of dimethylsebacate, 15.6 g of sodiumamide and 300 ml of diethyl ether was cooled, and 36 g of acetophenone was added dropwise at 0° to 5° C. After addition was completed, the whole was stirred at 0° to 5° C. for two hours, and held an additional two hours at room temperature. Water was added in a reactor, and the water layer was separated and neutralized. The resulting precipitate was recrystallized from acetone. The product was a white powder, melting point 108° to 111° C.

EXAMPLE III

Preparation of 1,4-bis(benzoylacetyl)methane

A mixture of 11.8 g of dimethylterephthalate, 15.6 g of sodium amide and 300 ml of diethyl ether was cooled, and 36 g of acetophenone was added dropwise at 0° to 5° C. After addition was completed, the whole was stirred at 0° to 5° C. for two hours, and held an additional two hours at room temperature. Water was added in a reactor, and the water layer was separated and neutralized. The resulting precipitate was recrystallized from acetone. The product was a white powder, melting point 173° to 176° C.

EXAMPLE IV

Preparation of zinc salt of 1,4-bis(benzoylacetyl)methane 7.4 g of 1,4-bis(benzoylacetyl)methane prepared in Example III was dissolved in 50 ml of benzene, and 10 g of 28% sodium methoxide (methanol solution) was added, and the mixture heated and stirred. The precipitated sodium salt was filtered, and dispersed in 100 ml of water, and then 2.7 g of zinc chloride was added and the mixture heated and stirred. The resulting precipitate was collected and dried. The product was a pale yellow powder, melting point more than 300° C., zinc content 14.8% (calculated: 15.1%).

The 1,3-dicarbonyl compounds of the invention are especially effective in enhancing the resistance to deterioration by heat and light of polyvinyl halide resins. The term "polyvinyl halide" as used herein is inclusive of any polymer formed at least in part of the recurring group:

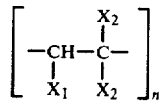

and having a halogen content in excess of 40%. In this group, X, is halogen: fluorine, chlorine or bromine, and the $X_2$ groups can each be either hydrogen or halogen, and n is the number of such units in the polymer chain. In polyvinyl fluoride, polyvinyl chloride and polyvinyl bromide homopolymers, each of the $X_2$ groups is hydrogen. Thus, the term includes not only polyvinyl fluoride, polyvinyl chloride and polyvinyl bromide homopolymers, but also after-halogenated polyvinyl halides as a class, for example, the after-chlorinated polyvinyl chlorides disclosed in British Pat. No. 893,288, and also polyvinylidene chloride, chlorinated polyethylene, chlorinated polypropylene, chlorinated rubber and copolymers of vinyl fluoride, vinyl chloride or vinyl bromide in a major proportion and other copolymerizable monomers in a minor proportion, such as copolymers of vinyl chloride and vinyl acetate, copolymers of vinyl chloride with acrylic or maleic or fumaric acids or esters, such as acrylic acid ester, maleic acid ester, methacrylic acid ester and acrylonitrile, and copolymers of vinyl chloride with styrene, ethylene, propylene, isobutene, vinylidene chloride, butadiene, isoprene; terpolymers of vinylchloride, styrene and acrylonitrile. The 1,3-dicarbonyl compounds are effective also with mixtures of polyvinyl halide in a major proportion with a minor proportion of other synthetic resins such as chlorinated polyethylene or a terpolymer of acrylonitrile, butadiene and styrene.

The 1,3-dicarbonyl compounds are applicable to the stabilization of rigid polyvinyl fluoride, polyvinyl chloride and polyvinyl bromide resin compositions, that is, polyvinyl halide resin compositions which are formulated to withstand high processing temperatures, of the order of 375° F. and higher, as well as plasticized polyvinyl halide resin compositions of conventional formulation, even though resistance to heat distortion is not a requisite. Conventional plasticizers well known to those skilled in the art can be employed such as, for example, dioctyl phthalate, octyl diphenyl phosphate and epoxidized soybean oil.

Particularly useful plasticizers are the epoxy higher esters having from 20 to 150 carbon atoms. Such esters will initially have had unsaturation in the alcohol or acid portion of the molecule, which is taken up by the formation of the epoxy group.

Typical unsaturated acids are acrylic, oleic, linoleic, linolenic, erucic, ricinoleic, and brassidic acids, and these may be esterified with organic monohydric or polyhydric alcohols, the total number of carbon atoms of the acid and the alcohol being within the range stated. Typical monohydric alcohols include butyl alcohol, 2-ethyl hexyl alcohol, lauryl alcohol, isooctyl alcohol, stearyl alcohol, and oleyl alcohol. The octyl alcohols are preferred. Typical polyhydric alcohols include pentaerythritol, glycerol, ethylene glycol, 1,2-propylene glycol, 1,4-butylene glycol, neopentyl glycol, ricinoleyl alcohol, erythritol, mannitol and sorbitol. Glycerol is preferred. These alcohols may be fully or partially esterified with the epoxidized acid. Also useful are the epoxidized mixtures of higher fatty acid esters found in naturally-occurring oils such as epoxidized soybean oil, epoxidized olive oil, epoxidized coconut oil, epoxidized cottonseed oil, epoxidized tall oil fatty acid esters and epoxidized tallow. Of these, epoxidized soybean oil is preferred. Also useful are epoxidized polybutadiene, methyl- butyl- or 2-ethylhexyl epoxy stearate, tris(epoxypropyl)isocyanurate, epoxidized castor oil, epoxidized safflower oil, 3-(2-xenoxy)-1,2-epoxypropane, Bisphenol A-polyglycidylether, vinylcyclohexene-di-epoxide, dicyclopentadiene di-epoxide and 3,4-epoxycyclohexylmethyl-3,4-epoxycyclohexane carboxylate.

The alcohol can contain the epoxy group and have a long or short chain, and the acid can have a short or long chain, such as epoxystearyl acetate, epoxystearyl stearate, glycidyl stearate, and polymerized glycidyl methacrylate.

The polyvinyl halide resin can be in any physical form, including, for example, powders, films, sheets, molded articles, foams, filaments, and yarns.

A sufficient amount of the 1,3-dicarbonyl compound is used to enhance the resistance of the polyvinyl halide to deterioration in physical properties, including, for example, discoloration and embrittlement, under the heat and/or light conditions to which the polymer will be subjected. Very small amounts are usually adequate. Amounts within the range from about 0.0001 to about 3% by weight of the polyvinyl halide resin are satisfactory. Preferably, an amount within the range from about 0.001 to about 1% is employed, for optimum stabilizing effectiveness.

The 1,3-dicarbonyl compounds of the invention can be employed as the sole stabilizer. They can also be used in combination with other conventional heat and light stabilizer for polyvinyl halide resins, in which combinations they show synergistic interaction, and provide an enhanced effectiveness, such as, for example, monovalent and polyvalent metal salts, alkaline earth metal phenolates, organic phosphites, and phenolic antioxidants, as well as 1,2-epoxy compounds, organotin compounds, thioethers, and ultraviolet light stabilizers.

The metal salts of carboxylic acids can be alkali metal salts, such as the lithium, sodium and potassium salts.

The polyvalent metal salts can be salts of any metal of Group II of the Periodic Table, such as zinc, calcium, cadmium, barium, magnesium and strontium, as well as tin, aluminum, zirconium and antimony.

The organic acid will ordinarily have from about six to about twenty-four carbon atoms, and can be any organic non-nitrogenous monocarboxylic acid. The aliphatic, aromatic, alicyclic and oxygen-containing heterocyclic organic acids are operable as a class. By the term "aliphatic acid" is meant any open chain carboxylic acid, substituted, if desired, with non-reactive groups, such as halogen, sulfur and hydroxyl. By the term "alicyclic" it will be understood that there is intended any cyclic acid in which the ring is nonaromatic and composed solely of carbon atoms, and such acids may if desired have inert, non-reactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkyl-substituted furoic acid. The aromatic acids likewise can have nonreactive ring substituents such as halogen, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, isooctoic acid, pelargonic acid, neodecanoic acid, capric acid, undecylic acid, lauric acid, myristic acid, palmitic acid, margaric acid, stearic acid, 12-hydroxystearic acid, oleic acid, ricinoleic acid, erucic acid, behenic acid, chlorocaproic acid, hydroxy capric acid, benzoic acid, phenylacetic acid, butyl benzoic acid, ethyl benzoic acid, isopropyl benzoic acid, hexyl benzoic acid, salicylic acid, 5-t-octyl salicylic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid, as well as partially esterified dibasic acids such as monobutylphthalate, isooctylmaleate and 2-ethoxyethyl maleate.

The water-insoluble salts are preferred, because they are not leached out when the plastic is in contact with water. Where these salts are not known, they are made by the usual types of reactions, such as by mixing the acid, or anhydride with the corresponding oxide or hydroxide of the metal in a liquid solvent, and heating, if necessary, until salt formation is complete.

Instead of or together with the above metal salts of organic acids, a metal salt of a phenol or hydrocarbon-substituted phenol can be used. Among such metal phenolates there can be mentioned salts of any of the above monovalent and polyvalent metals with phenol, cresol, ethylphenol, xylenol, butylphenol, isoamylphenol, isooctylphenol, t-nonylphenol, decylphenol, dodecylphenol, t-octylphenol, cyclohexylphenyl, di-t-nonylphenol, methyl isohexyl phenol, phenylphenol.

A variety of organic triphosphites and acid phosphites can be employed, of which the following are exemplary.

The organic triphosphite can be any organic phosphite having three or more organic radicals attached to phosphorus through oxygen. The acid phosphite can be any organic phosphite having one or two organic radicals attached to phosphorus through oxygen. These radicals can be monovalent radicals, in the case of the triphosphites, diphosphites and monophosphites.

The organic triphosphites in which the radicals are monovalent radicals can be defined by the formula:

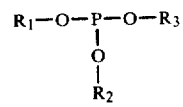

in which
$R_1$, $R_2$ and $R_3$ are selected from the group consisting of alkyl, alkenyl, aryl, alkaryl, aralkyl, and cycloalkyl groups having from one to about thirty carbon atoms.

The acid phosphites are defined by the same formula, but one or two of $R_1$, $R_2$ and $R_3$ is hydrogen or a cation of a metal or ammonium.

Also included are the organic triphosphites having a bivalent organic radical forming a heterocyclic ring with the phosphorus of the type:

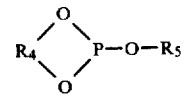

in which $R_4$ is a bivalent organic radical selected from the group consisting of alkylene, arylene, aralkylene, alkarylene and cycloalkylene radicals having from two to about thirty carbon atoms, and $R_5$ is a monovalent organic radical as defined above in the case of $R_1$, $R_2$ and $R_3$.

$R_5$ is hydrogen or a cation, in the case of the acid phosphites.

Also useful organic triphosphites are mixed heterocyclic-open chain phosphites of the type:

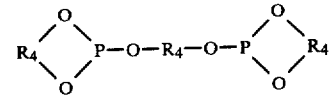

More complex triphosphites are formed from trivalent organic radicals, of the type:

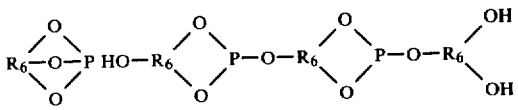

in which $R_6$ is a trivalent organic radical of any of the types of $R_1$ to $R_5$, inclusive, as defined above.

A particularly useful class of complex triphosphites are the tetraoxadiphosphaspiro undecanes of the formula:

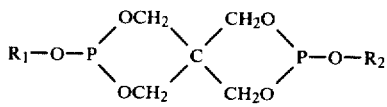

where $R_1$ and $R_2$ are selected from the group consisting of aryl, alkyl, aryloxyethyl, alkyloxyethyl, aryloxyethoxyethyl, alkyloxyethoxyethyl and alkyloxypolyethoxyethyl having from about one to about thirty carbon atoms.

In the case of the acid phosphites, one or both of $R_1$ and $R_2$ is also hydrogen or a cation.

An especially preferred class of organic triphosphites and acid phosphites have a bicyclic aromatic group attached to phosphorus through oxygen, with no or one or more phenolic hydroxyl groups on either or both of the aromatic rings. These phosphites are characterized by the formula:

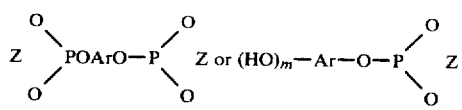

in which Ar is a mono or bicyclic aromatic nucleus and m is an integer of from 0 to 5. Z is one or a plurality of organic radicals as defined above for $R_1$ to $R_6$, taken singly or together in sufficient number to satisfy the valences of the two phosphite oxygen atoms.

One or both Z radicals is also hydrogen, in the case of the acid phosphites, and can include additional bicyclic aromatic groups of the type $(HO)_m$—Ar.

The cation in the case of acid phosphites can be a metal, such as an alkali metal, for instance, sodium, potassium or lithium; an alkaline earth metal, for instance, barium, calcium, or a nontoxic polyvalent metal, such as magnesium, tin and zinc.

Usually, the triphosphites and acid phosphites will not have more than about sixty carbon atoms.

Exemplary triphosphites are monophenyl di-2-ethylhexyl phosphite, diphenyl mono-2-ethylhexyl phosphite, di-isooctyl monotolyl phosphite, tri-2-ethylhexyl phosphite, phenyl dicyclohexyl phosphite, phenyl diethyl phosphite, triphenyl phosphite, tricresyl phosphite, tri(dimethylphenyl)phosphite, trioctadecyl phosphite, triisooctyl phosphite, tridodecyl phosphite, isooctyl diphenyl phosphite, diisooctyl phenyl phosphite, tri(t-octylphenyl)phosphite, tri(t-nonylphenyl)phosphite, benzyl methyl isopropyl phosphite, butyl dicresyl phosphite, isooctyl di(octylphenyl)phosphite, di(2-ethylhexyl)(isooctylphenyl)phosphite, tri(2-phenylethyl)phosphite, ethylene phenyl phosphite, ethylene isohexyl phosphite, ethylene isooctyl phosphite, ethylene cyclohexyl phosphite, 2-phenoxy-5,5-dimethyl-1,3,2-dioxaphosphorinane, 2-butoxy-1,3,2-dioxyphosphorinane, 2-octoxy-5,5-dimethyldioxaphosphorinane, and 2-cyclohexyloxy-5,5-diethyl dioxaphosphorinane.

Exemplary pentaerythritol triphosphites are 3,9-diphenoxy-2,4,8,10-tetraoxa-3,9-diphosphaspiro-(5,5)-undecane(diphenyl-pentaerythritol-diphosphite), 3,9-di(decyloxy)-2,4,8,10-tetraoxa-3,9-diphosphaspiro(5,5)-undecane, 3,9-di(isodecyloxy)-2,4,8,10-tetraoxa-3,9-diphosphaspiro-(5,5)-undecane, 3-phenoxy-9-isodecyloxy-2,4,8,10-tetraoxa-3,9-diphosphaspiro-(5,5)-undecane, 3,9-di(methoxy)-2,4,8,10-tetraoxa-3,9-diphosphaspiro-(5,5)-undecane, 3,9-di(lauryloxy)-2,4,8,10-tetra oxa-3,9-diphosphaspiro-(5,5)-undecane, 3,9-di-p-tolyloxy-2,4,8,10-tetraoxa-3,9-diphosphaspiro-(5,5)-undecane; 3,9-di(methoxyethyloxy)-2,4,8,10-tetraoxa-3,9-diphosphaspiro-(5,5)-undecane; 3-methoxyethyloxy-9-isodecyloxy-2,4,8,10-tetraoxa-3,9-diphosphaspiro-(5,5)-undecane; 3,9-di(ethoxyethyloxy)-2,4,8,10-tetraoxa-3,9-diphosphaspiro-(5,5)-undecane; 3,9-di(butoxyethyloxy)-2,4,8,10-tetraoxa-3,9-diphosphaspiro-(5,5)-undecane; 3-methoxyethyloxy-9-butoxyethyloxy-2,4,8,10-tetraoxa-3,9-diphosphaspiro-(5,5)-undecane; 3,9-di(methoxyethoxyethyloxy) 2,4,8,10-tetraoxa-3,9-diphosphaspiro-(5,5)-undecane; 3,9-di(butoxyethoxyethyloxy)-2,4,8,10-tetraoxa-3,9-diphosphaspiro-(5,5)-undecane; 3,9-di(methoxyethoxyethoxyethyloxy)-2,4,8,10-tetraoxa-3,9-diphosphaspiro-(5,5)-undecane; 3,9-di(methoxy(polyethoxy)ethyloxy)-2,4,8,10-tetraoxa-3,9-diphosphaspiro (5,5)-undecane (where the (polyethoxy)ethyloxy group has an average molecular weight of 350)3,9-di(methoxy(polyethoxy)ethyloxy)-2,4,8,10-tetraoxa-3,9-diphosphaspiro-(5,5)-undecane (where the (polyethoxy)ethyloxy group has an average molecular weight of 550).

Exemplary of the bis aryl triphosphites are: bis(4,4'-thio-bis(2-tertiary butyl-5-methyl-phenol))isooctyl phosphite, mono(4,4'-thio-bis(2-tertiary-butyl-5-methyl phenol))di-phenyl phosphite, tri(4,4'-n-butylidene-bis(2-tertiary-butyl-5-methylphenol))phosphite, (4,4'-benzylidene-bis(2-tertiary-butyl-5-methyl phenol))diphenyl phosphite, isooctyl 2,2'-bis(-parahydroxyphenyl)propane phosphite, decyl 4,4'-n-butylidene-bis(2(tertiary-butyl-5-methylphenol)phosphite, tri-4,4'-thio-bis(2-tertiary-butyl-5-methylphenol)phosphite, 2-ethylhexyl-2,2'-methylene-bis-(4-methyl-6,1'-methylcyclohexyl)-phenol phosphite, tri(2,2'-bis(para-hydroxyphenyl)-propane)phosphite, tri(4,4'-thio-bis(2-tertiary-butyl-5-methyl-phenol) phosphite, isooctyl-(2,6-bis(2'-hydroxy-3,5-dinonylbenzyl)-4-nonyl phenyl))phosphite, tetratridecyl 4,4'-n-butylidene-bis(2-tertiary butyl-5-methyl phenyl)diphosphite, tetra-isooctyl 4,4'-thio-bis(2-tertiary butyl-5-methyl phenyl)diphosphite, 2,2'-methylene-bis(4-methyl 6,1'-methyl cyclohexyl phenyl)polyphosphite, isooctyl-4,4'-isopropylidene-bis-phenyl-polyphosphite, 2-ethylhexyl-2,2'-methylene-bis(4-methyl-6,1'-methyl-cyclohexyl)phenyl triphosphite, tetratridecyl-4,4'-oxydiphenyl diphosphite, tetra-n-dodecyl-4,4'-n-butylidene bis(2-tertiary-butyl-5-methylphenyl) diphosphite, tetra-tridecyl-4,4'-iso-propylidene bisphenyl diphosphite, hexatridecyl butane-1,1,3-tris(2'-methyl-5'-tertiary-butylphenyl-4'-)triphosphite.

Exemplary acid phosphites are di(phenyl)phosphite, monophenyl phosphite, mono-(diphenyl)phosphite, dicresyl phosphite, di-o-(isooctylphenyl)phosphite, di(p-ethylhexylphenyl) phosphite, di(p-t-octylphenyl) phosphite, di(dimethylphenyl) phosphite, di-n-butyl phosphite, di-2-ethylhexyl phosphite, mono-2-ethylhexyl phosphite, diisooctyl phosphite, monoisooctyl phosphite, monododecyl phosphite, 2-ethylhexyl phenyl phosphite, 2-ethylhexyl-(n-octylphenyl)phosphite, monocyclohexyl phosphite, dicyclohexyl phosphite, di(2-cyclohexyl phenyl)phosphite, di-α-naphthyl phosphite, diphenyl phenyl phosphite, di(diphenyl)phosphite, di-(2-phenyl ethyl)phosphite, dibenzyl phosphite, monobenzyl phosphite, n-butyl cresyl phosphite and didodecyl phosphite, cresyl phosphite, t-octylphenyl phosphite, ethylene phosphite, butyl cresyl phosphite, isooctyl monotolyl phosphite and phenyl cyclohexyl phosphite.

Exemplary of the bis aryl acid phosphites are: bis(4,4'-thio-bis(2-tertiary-butyl-5-methyl-phenol))-phosphite, (4,4'-thio-bis(2-tertiary-butyl-5-methyl-phenol))phenyl phosphite, bis(4,4'-n-butylidene-bis(2-tertiary-butyl-5-methyl-phenol))phosphite, mono(4,4'-benzylidene-bis(2-tertiary-butyl-5-methyl-phenol))phosphite, mono(2,2'-bis-(parahydroxyphenyl)-propane)phosphite, mono(4,4'-n-butylidene-bis(2-tertiary-butyl-5-methyl-phenol)phosphite, bis(4,4'-thio-bis(2-tertiary-butyl-5-methylphenol))phosphite, mono-2-ethylhexyl-mono-2,2'methylene-bis(4-methyl-6,1'methylcyclohexyl)phenol phosphite, bis(2,2'-bis-(parahydroxyphenyl)propane)phosphite, monoisooctyl mono(4,4'-thio-bis(2-tertiary-butyl-5-methyl-phenol))-phosphite, isooctyl-(2,6-bis(2'-hydroxy-3,5-dinonylbenzyl)-4-nonyl phenyl))phosphite, tri-tridecyl 4,4'-n-butylidene-bis(2-tertiary-butyl-5-methyl phenyl)diphosphite, triisooctyl 4,4'-thio-bis(2-tertiary-butyl-5-methyl phenyl)diphosphite, bis(2,2'-methylene-bis(4-methyl-6,1'-methyl cyclohexyl phenyl))phosphite, isooctyl-4,4'-isopropylidene bis-phenyl phosphite, monophenyl mono(2,2'-methylene-bis-(4-methyl-6,1'-methyl-cyclohexyl)) triphosphite, di-tridecyl-4,4'-oxydiphenyl diphosphite, di-n-dodecyl-4,4'-n-butylidene bis(2-tertiary-butyl-5-methylphenyl)diphosphite, di-tridecyl-4,4'-isopropylidene bisphenyl diphosphite, tetra-tridecyl butane-1,1,3-tris(2'-methyl-5'-tertiary-butylphenyl-4-)triphosphite.

The phenolic antioxidant contains one or more phenolic hydroxyl groups, and one or more phenolic nuclei, and can contain from about eight to about three hundred carbon atoms. In addition, the phenolic nucleus can contain an oxy or thio ether group.

The alkyl-substituted phenols and polynuclear phenols, because of their molecular weight, have a higher boiling point, and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatability with polypropylene, inasmuch as the phenolic compound then acquires more of an aliphatic hydrocarbon character, and therefore there is no upper limit on the number of alkyl carbon atoms. Usually, from the standpoint of availability, the compound will not have more than about eighteen carbon atoms in an alkyl, alicyclidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In the case of bicyclic phenols, the rings can be linked by thio or oxyether groups, or by alkylene, alicyclidene or arylidene groups.

The monocyclic phenols which can be employed have the structure:

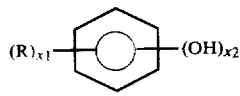

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and acyl

where R' is aryl, alkyl or cycloalkyl;

$x_1$ and $x_2$ are integers from one to four, and the sum of $x_1$ and $x_2$ does not exceed six.

The polycyclic phenol employed in the stabilizer combination is one having at least two aromatic nuclei linked by a polyvalent linking radical, as defined by the formula:

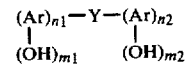

wherein Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms.

Ar is a phenolic nucleus which can be a phenyl or a polycarbocyclic group having condensed or separate phenyl rings; each Ar group contains at least one free phenolic hydroxyl group up to a total of five. The Ar rings can also include additional rings connected by additional linking nuclei of the type Y, for example, Ar—Y—Ar—Y—Ar.

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen, halogen atoms, e.g., chlorine, bromine and fluorine; organic radicals containing from one to about thirty carbon atoms, such as alkyl, aryl, alkaryl, aralkyl, cycloalkenyl, cycloalkyl, alkoxy, aryloxy and acyloxy

where R' is aryl, alkyl or cycloalkyl, or thiohydrocarbon groups having from one to about thirty carbon atoms, and carboxyl

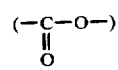

groups. Usually, however, each aromatic nucleus will not have more than about eighteen carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluorenyl groups.

When Ar is a benzene nucleus, the polyhydric polycyclic phenol has the structure:

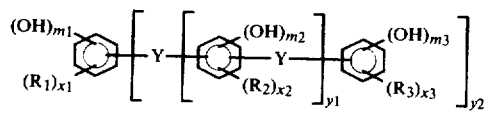

wherein
R₁, R₂ and R₃ are inert substituent groups as described in the previous paragraph;
m₁ and m₃ are integers from one to a maximum of five;
m₂ is an integer from one to a maximum of four;
x₁ and x₃ are integers from zero to four; and
x₂ is an integer from zero to three;
y₁ is an integer from zero to about six; and
y₂ is an integer from one to five, preferably one or two.

Preferably, the hydroxyl groups are located ortho and/or para to Y.

Exemplary Y groups are alkylene, alkylidene, and alkenylene arylene, alkylarylene, arylalkylene, cycloalkylene, cycloalkylidene, and oxa- and thia-substituted such groups; carbonyl groups, tetrahydrofuranes, esters and triazino groups. The Y groups are usually bi, tri, or tetravalent, connecting two, three or four Ar groups. However, higher valency Y groups, connecting more than four Ar groups can also be used. According to their constitution, the Y groups can be assigned to subgenera as follows:

(1) Y groups where at least one carbon in a chain or cyclic arrangement connect the aromatic groups, such as:

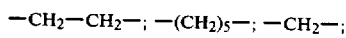

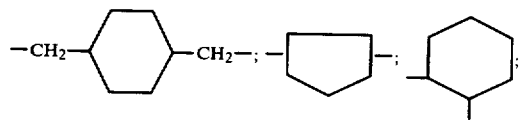

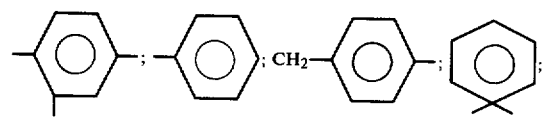

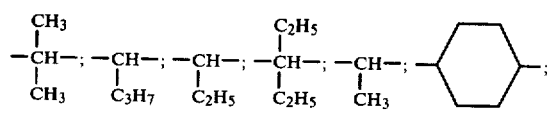

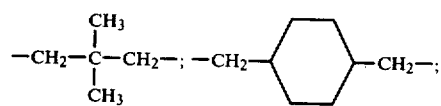

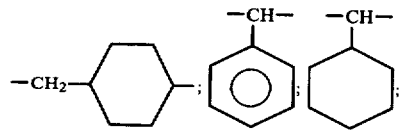

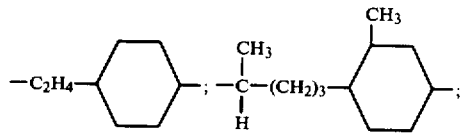

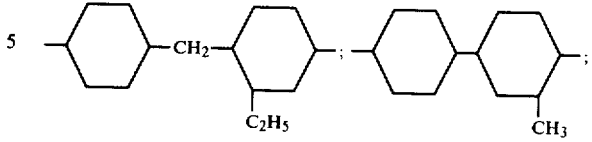

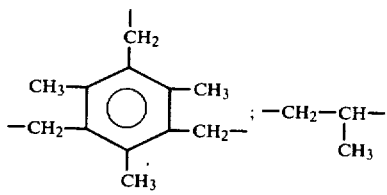

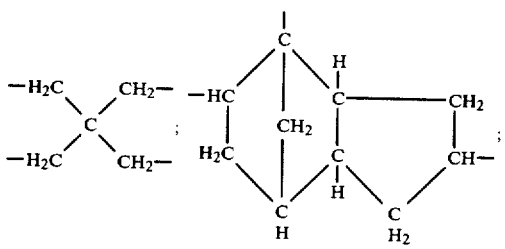

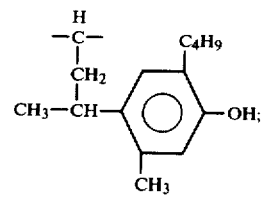

(2) Y groups where only atoms other than carbon link the aromatic rings, such as:

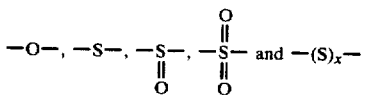

where x is a number from one to ten;

(3) Y groups made up of more than a single atom including both carbon and other atoms linking the aromatic nuclei, such as:

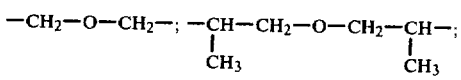

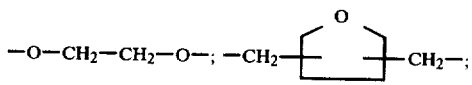

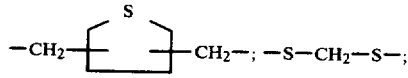

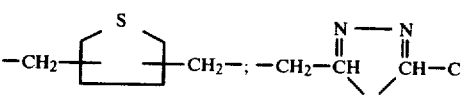

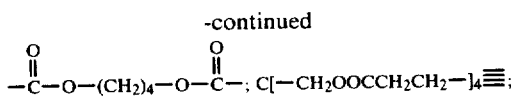

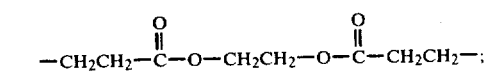

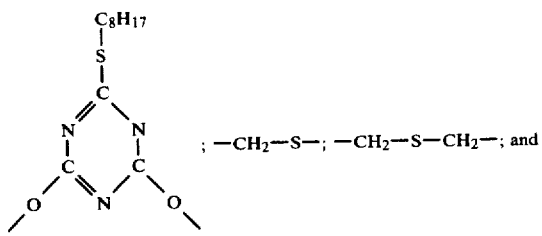

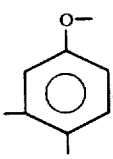

Although the relation of effectiveness to chemical structure is insufficiently understood, many of the most effective phenols have Y groups of subgenus (1), and accordingly this is preferred. Some of these phenols can be prepared by the alkylation of phenols or alkyl phenols with polyunsaturated hydrocarbons such as dicyclopentadiene or butadiene.

Representative phenols include guaiacol, resorcinol monoacetate, vanillin, butyl salicylate, 2,6-di-tert-butyl-4-methyl phenol, 2-tert-butyl-4-methoxy phenol, 2,4-dinonyl phenol, 2,3,4,5-tetradecyl phenol, tetrahydro-α-naphthol, o-, m- and p-cresol, o-, m- and p-phenyl-phenol, o-, m- and p-xylenols, the carvenols, symmetrical xylenol, thymol, o-, m- and p-nonylphenol, o-, m- and p-dodecyl-phenol, and o-, m- and p-octyl phenol, o-, and m-tert-butyl-p-hydroxy-anisole, p-n-decyloxy-phenol, p-n-decyloxycresol, nonyl-n-decyloxy-cresol, eugenol, isoeugenol, glyceryl monosalicylate, methyl-p-hydroxy-cinnamate, 4-benzyloxy-phenol, p-acetylaminophenol, p-stearyl-aminophenol methyl-p-hydroxy benzoate, p-di-chlorobenzyl-aminophenol, p-hydroxysalicyl anilide, stearyl-(3,5-di-methyl-4-hydroxy-benzyl)thioglycolate, stearyl-β-(4-hydroxy-3,5-di-t-butylphenyl)propionate, distearyl-3,5-di-t-butyl-4-hydroxybenzylphosphonate, and distearyl (4-hydroxy-3-methyl-5-t-butyl)benzylmalonate.

Exemplary polyhydric phenols are orcinol, propyl gallate, catechol, resorcinol, 4-octyl-resorcinol, 4-dodecyl-resorcinol, 4-octadecyl-catechol, 4-isooctyl-phloroglucinol, pyrogallol, hexahydroxybenzene, 4-isohexyl-catechol, 2,6-di-tertiary-butylresorcinol, 2,6-di-isopropyl-phloroglucinol.

Exemplary polyhydric polycyclic phenols are methylene bis-(2,6-di-tertiary-butyl-phenol), 2,2-bis-(4-hydroxy phenyl)propane, methylene-bis-(p-cresol), 4,4'-benzylidene bis-(2-tertiary-butyl-5-methyl-phenol), 4,4'-cyclohexylidene bis-(2-tertiary-butylphenol), 2,2'-methylene-bis-(4-methyl-6-(1'-methyl-cyclohexyl)-phenol), 2,6-bis-(2'-hydroxy-3'-tertiary-butyl-5'-methyl-benzyl)-4-methylphenol, 4,4'-bis-(2-tertiary-butyl-5-methyl-phenol), 2,2'-bis-(4-hydroxy-phenyl)butane, ethylene bis(p-cresol), 4,4'-oxobis-phenol, 4,4'-oxobis (3-methyl-5-isopropylphenol), 4,4'-oxobis-(3-methyl-phenol), 2,2'-oxobis-(4-dodecylphenol), 2,2'-oxobis-(4-methyl-5-tertiary-butyl-phenol), 4,4'-thio-bis-phenol; 4,4'-thio-bis-(3-methyl-6-tertiary-butyl-phenol), 2,2'-thio-bis-(4-methyl-6-tertiary-butyl-phenol), 4,4'-n-butylidene-(2-t-butyl-5-methyl-phenol), 2,2'-methylene-bis-(4-methyl-6-(1'-methyl-cyclohexyl)-phenol), 4,4'-cyclohexylene bis(2-tertiary-butyl-phenol), 2,6-bis-(2'-hydroxy-3'-t-butyl-5'-methyl-benzyl)-4-methyl-phenol, 4,4'-oxobis (naphthalene-1,5-diol), 1,3'-bis-(naphthalene-2,5-diol)propane, and 2,2'-butylene bis-(naphthalene-2,7-diol), (3-methyl-5-tert-butyl-4-hydroxy-phenyl)-4'-hydroxy-phenyl propane, 2,2'-methylene-bis-(4-methyl-5-isopropylphenol), 2,2'-methylene bis-(5-tert-butyl-4-chlorophenol), (3,5-di-tert-butyl-4-hydroxyphenyl)-(4'-hydroxy-phenyl)ethane, (2-hydroxyphenyl)-(3',5'-di-tert-butyl-4',4-hydroxyphenyl) ethane, 2,2'-methylene bis-(4-octylphenol), 4,4'-propylene bis-(2-tert-butyl-phenol), 2,2'-isobutylene bis-(4-nonyl-phenol), 2,4-bis-(4-hydroxy-3-t-butyl-phenoxy)-6-(n-octylthio)-1,3,5-triazine, 2,4,6-tris-(4-hydroxy-3-t-butyl-phenoxy)-1,3,5-triazine, 2,2'-bis-(3-t-butyl-4-hydroxyphenyl)thiazolo-(5,4-d)thiazole, 2,2'-bis-(3-methyl-5-t-butyl-4-hydroxyphenyl)thiazolo-(5,4-d)-thiazole, 4,4'-bis-(4-hydroxy-phenyl)pentanoic acid octadecyl ester, cyclopentylene-4,4'-bis-phenol, 2-ethylbutylene-4,4'-bisphenol, 4,4'-cyclooctylene-bis-(2-cyclohexyl-phenol),β,β-thiodiethanol bis-(3-tert-butyl-4-hydroxy-phenoxy acetate), 1,4-butanedio bis-(3-tert-butyl-4-hydroxyphenoxy acetate), pentaerythritoltetra (4-hydroxyphenol propionate), 2,4,4'-tri-hydroxy benzophenone, bis-(2-tert-butyl-3-hydroxy-5-methylphenyl)-sulfide, bis-(2-tert-butyl-4-hydroxy-5-methylphenyl)sulfide, bis-(2-tert-butyl-4-hydroxy-5-methyl-phenyl sulfoxide), bis-(3-ethyl-5-tert-butyl-4-hydroxy benzyl)sulfide, bis-(2-hydroxy-4-methyl-6-tert-butyl phenyl) sulfide, 4,4'-bis-(4-hydroxy-phenol)pentanoic acid octadecyl thiopropionate ester, 1,1,3-tris-(2'-methyl-4-hydroxy-5'-tert-butylphenyl)butane, 1,1,3-tris-(1-methyl-3-hydroxy-4-tert-butylphenyl)butane, 1,8-bis-(2-hydroxy-5-methylbenzoyl-n-octane, 2,2'-ethylene-bis-[4'-(3-tert-butyl-4-hydroxyphenyl)thiazole], 1-methyl-3-(3-methyl-5-tert-butyl-4-hydroxybenzyl)-naphthalene, 2,2'-(2-butene)-bis-(4-methoxy-6-tert-butyl phenol)-bis-[3,3-bis-(4-hydroxy-3-t-butylphenyl)butyric acid] glycol ester,4,4'-butylidene-bis-(6-t-butyl-m-cresol), 1,1,3-tris-(2-methyl-4-hydroxy-5-t-butylphenyl)butane, 1,3,5-tris-(3,5-di-t-butyl-4-hydroxybenzyl)-2,4,6-trimethylbenzene, tetrakis[methylene-3-(3,5-di-t-butyl-4-hydroxyphenyl)propionate] methane, 1,3,5-tris-(3,5-di-t-butyl-4-hydroxybenzyl)isocyanurate, 1,3,5-tris-(3,5-di-t-butyl-4-hydroxyphenyl)propionyl-oxyethyl isocyanurate, 2-octylthio-4,6-di-(4-hydroxy-3,5-di-t-butyl) phenoxy-1,3,5-triazine, 4,4'-thiobis(6-t-butyl-m-cresol) and pentaerythritol hydroxyphenyl propionate.

A particularly desirable class of polyhydric polycyclic phenols are the dicyclopentadiene polyphenols, which are of the type:

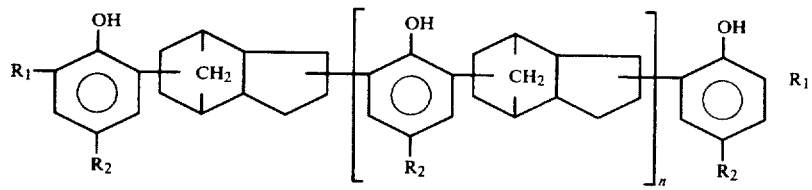

in which
- R₁ and R₂ are lower alkyl, and can be the same or different, and
- n is the number of the groups enclosed by the brackets, and is usually from 1 to about 5. These are described in U.S. Pat. No. 3,567,683, dated Mar. 2, 1971 to Spacht. A commercially available member of this class is Wingstay L, exemplified by dicyclopentadiene tri-(2-tert-butyl-4-methyl-phenol) of the formula:

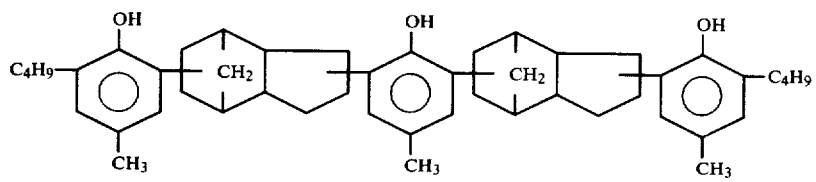

The polyhydric polycyclic phenols used in the invention can also be condensation products of phenol or alkylphenols with hydrocarbons having a bicyclic ring structure and a double bond or two or more double bonds, such as α-pinene, β-pinene, dipentene, limonene, vinylcyclohexene, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertain, the Y groups linking the phenolic nuclei all fall into the preferred subgenus (1). For method of preparation, see e.g., U.S. Pat. Nos. 3,124,555, 3,242,135 and British Pat. No. 961,504.

In addition, any of the conventional polyvinyl halide resin additives, such as lubricants, emulsifiers, antistatic agents, flame-proofing agents, pigments and fillers, can be employed.

The stabilizer system is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polyvinyl halide resin can be worked into the desired shape, such as by milling, calendering, extrusion or injection molding, or fiber-forming. In such operations, it will be found to have a considerably improved resistance to discoloration and embrittlement on exposure to heat and light.

A sufficient amount of the 1,3-dicarbonyl compound and any stabilizer combination including the 1,3-dicarbonyl compound is used to improve the resistance of the resin to deterioration in physical properties, including, for example, discoloration, reduction in melt viscosity and embrittlement, under the conditions to which the resin will be subjected. Very small amounts are usually adequate. Amounts within the range from about 0.0001 to about 10% total stabilizers by weight of the polymer are satisfactory. Preferably, from 0.01 to 5% is employed for optimum stabilization. Oxirane or 1,2-epoxide stabilizers can be included in amounts corresponding to 0.01 to 10% by weight and organic phosphites in amounts within the range from about 0.01 to 5% by weight.

The following Examples illustrate preferred stabilizer systems and resin compositions of the invention:

EXAMPLES 1 TO 10

A group of polyvinyl chloride resin compositions was prepared having the following formulation:

| Ingredient | Parts by Weight |
| --- | --- |
| Polyvinyl chloride (Geon 103 EP) | 100 |
| Dioctyl phthalate | 50 |
| Epoxidized soybean oil | 3.0 |
| Ca stearate | 1.0 |
| Zn stearate | 0.3 |
| Stearic acid | 0.3 |
| Tris(nonylphenyl) phosphite | 0.5 |
| 1,3-Dicarbonyl compound shown in Table I | 0.1 |

This formulation was blended and sheeted off on a two-roll mill to form sheets 1 mm thick.

The sheets were heated in air in a Geer oven at 190° C. to evaluate heat stability, and the time in minutes noted for the sheet to develop a noticeable discoloration and/or embrittlement. Initial color and color after heating at 190° C. were also measured, using a Hunter color difference meter to determine the amount of yellowness on a scale where the higher the numerical value, the more yellow the sample is, and the clarity of the sheet was also observed. Plate-out was also measured on a scale where the higher the numerical value the more the plate-out.

The results are shown in Table I.

TABLE I

| Example No. | 1,3-Dicarbonyl Compound | Heat Stability (Minutes) | Initial Color | Clarity | Heat Color | Plate-Out |
|---|---|---|---|---|---|---|
|  | None | 35 | 33 | Medium | 65 | 150 |
| Control 1 | Dibenzoylmethane | 45 | 17 | Good | 39 | 130 |
| Control 2 | Benzoylacetylmethane | 45 | 20 | Good | 42 | 120 |
| 1 | 1,4-Dibenzoyl-butane-2,3-dione | 55 | 12 | Very Good | 18 | 25 |
| 2 | 1,5-Dibenzoyl-pentane-2,4-dione | 60 | 10 | Very Good | 17 | 30 |
| 3 | 1,12-Dibenzoyl-dodecane-2,11-dione | 65 | 8 | Very Good | 12 | 10 |
| 4 | 1,3-Bis(benzoyl-acetyl)benzene | 65 | 8 | Very Good | 13 | 15 |
| 5 | 1,4-Bis(aceto-acetyl)benzene | 55 | 11 | Good | 17 | 25 |
| 6 | 1,7-Dibenzoyl-4-thiaheptane-2,6-dione | 60 | 11 | Very Good | 16 | 20 |
| 7 | 1,1-Bis(benzoyl-acetylethylthio)cyclohexane | 65 | 9 | Very Good | 13 | 10 |
| 8 | N,N,N—Tris(benzoylacetylethyl)amine | 70 | 12 | Good | 17 | 30 |
| 9 | Zn[1,3-Bis(benzoylacetyl)benzene]$_2$ | 55 | 7 | Very Good | 14 | 20 |
| 10 | Ba[1,4-Bis(acetoacetyl)benzene]$_2$ | 60 | 12 | Good | 16 | 30 |

The results demonstrate the surprising improvement in each of the five properties evaluated with the stabilizers according to this invention, as compared to the controls.

EXAMPLES 11 TO 23

A group of polyvinyl chloride resin compositions was prepared having the following formulation:

| Ingredient | Parts by Weight |
|---|---|
| Polyvinyl chloride (Geon 103 EP) | 100 |
| Epoxidized soybean oil | 3.0 |
| Ba stearate | 0.3 |
| Ba nonyl phenate | 0.5 |
| Zn toluate | 0.5 |
| Stearic acid | 0.3 |
| Octyl diphenyl phosphite | 1.0 |
| 1,3-Dicarbonyl compound shown in Table II | 0.1 |

This formulation was blended and sheeted off on a two-roll mill to form sheets 1 mm thick.

The sheets were heated in air in a Geer oven at 190° C. to evaluate heat stability, and the time in minutes noted for the sheet to develop a noticeable discoloration and/or embrittlement. Initial color was measured in a Hunter color difference meter, to determine degree of yellowness, as well as color after heating at 190° C. for thirty minutes.

The results are shown in Table II.

TABLE II

| Example No. | 1,3-Dicarbonyl Compound | Heat Stability (minutes) | Initial Color | Heat Color |
|---|---|---|---|---|
|  | None | 40 | 25 | 47 |
| Control 1 | Benzoylacetone | 45 | 14 | 27 |
| Control 2 | (Benzoylacetone)$_2$ Ca | 50 | 18 | 38 |
| 11 | 2,7-Dibenzoyloctane-3,6-dione | 80 | 12 | 17 |
| 12 | 1,8-Bis(2-hydroxy-benzoyl)octane-2,7-dione | 90 | 9 | 15 |
| 13 | 1,4-Bis(benzoyl-acetyl)benzene | 85 | 11 | 17 |
| 14 | 1,3-Bis(acetoacetyl)benzene | 85 | 10 | 15 |
| 15 | 1,9-Dibenzoyl-5-thianonane-2,8-dione | 80 | 10 | 16 |
| 16 | 1,9-Dibenzoyl-4,6-dithianonane-2,8-dione | 75 | 12 | 18 |
| 17 | N,N—Bis(benzoylacetyl-methyl)methylamine | 75 | 11 | 16 |
| 18 | 2,3-Bis(benzoylacetyl)bicyclo(2,2,1)heptene-5 | 85 | 9 | 15 |
| 19 | 1,2,4-Tris(benzoyl-acetyl)benzene | 80 | 10 | 17 |
| 20 | Zn[1,12-Dibenzoyl-dodecane-2,11-dione]$_2$ | 80 | 8 | 14 |
| 21 | Zn[1,4-Bis(benzoyl-acetyl)benzene]$_2$ | 80 | 10 | 16 |
| 22 | Ca[1,3-Bis(acetoacetyl)benzene]$_2$ | 85 | 11 | 15 |
| 23 | (C$_4$H$_9$)$_2$Sn—[2,3-Bis-(benzoylacetyl)bicyclo(2,2,1)heptene-5]$_2$ | 95 | 9 | 14 |

The results demonstrate the surprising improvement obtained in color and heat stability with compositions of this invention compared to the Controls.

EXAMPLES 24 TO 36

A group of polyvinyl chloride resin compositions was prepared having the following formulation:

| Ingredient | Parts by Weight |
|---|---|
| Polyvinyl chloride (Geon 103 EP) | 100 |
| Acrylonitrile-butadiene-styrene terpolymer (Blendex 111) | 10 |
| Dioctyl phthalate | 10 |
| Ca benzoate | 1.0 |

| Ingredient | Parts by Weight |
| --- | --- |
| Stearic acid | 0.5 |
| Zn octoate | 0.4 |
| Tetra (C$_{12-15}$alkyl)Bisphenol A diphosphite | 1.0 |
| 1,3-Dicarbonyl compound as shown in Table III | 0.005 |

This formulation was blended and sheeted off on a two-roll mill to form sheets 1 mm thick.

The sheets were heated in a Geer oven at 175° C. to evaluate heat stability, and the time in minutes noted for the sheet to develop a noticeable discoloration and/or embrittlement. Initial color and color after heating at 175° C. for sixty minutes was also noted using a Hunter color difference meter.

The results obtained are given in Table III.

TABLE III

| Example No. | 1,3-Dicarbonyl Compound | Heat Stability (minutes) | Initial Color | Heat Color |
| --- | --- | --- | --- | --- |
| | None | 95 | 28 | 45 |
| Control 1 | Dibenzoylmethane | 105 | 16 | 22 |
| Control 2 | [Dibenzoylmethane]$_2$-Zn | 100 | 14 | 23 |
| Control 3 | 1,4-Bis(diacetylmethyl)benzene | 100 | 21 | 34 |
| 24 | 1,4-Dibenzoylbutane-2,3-dione | 135 | 10 | 15 |
| 25 | 1,12-Dibenzoyldodecane-2,11-dione | 160 | 8 | 12 |
| 26 | 1,6-Dibenzoyl-3-hexene-2,5-dione | 140 | 11 | 17 |
| 27 | 1,3-Bis(benzoylacetyl)benzene | 155 | 8 | 13 |
| 28 | 1,4-Bis(acetoacetyl)benzene | 135 | 10 | 16 |
| 29 | 1,4-Bis(2-ketocyclohexanoyl)benzene | 120 | 12 | 17 |
| 30 | 1,7-Dibenzoyl-4-oxaheptane-2,6-dione | 130 | 12 | 16 |
| 31 | 1,1-Bis(benzoylacetylethylthio)cyclohexane | 150 | 9 | 14 |
| 32 | 1,2,3-Tris(benzoylacetyl)butane | 135 | 11 | 15 |
| 33 | 1,1,2,2-Tetrakis(benzoylacetyl)ethylene | 140 | 12 | 16 |
| 34 | Ba[1,12-Dibenzoyldodecane-2,11-dione]$_2$ | 160 | 9 | 13 |
| 35 | Zn[1,3-Bis(benzoylacetyl)benzene]$_2$ | 150 | 7 | 11 |
| 36 | Na[1,1-Bis(benzoylacetylethylthio)cyclohexane] | 140 | 11 | 16 |

The results demonstrate the surprising advantage in color protection and heat stability using the stabilizers of this invention as compared to the Controls.

EXAMPLES 37 TO 47

A group of polyvinyl chloride resin compositions was prepared having the following formulation:

| Ingredient | Parts by weight |
| --- | --- |
| Polyvinyl chloride | 100 |
| Dioctyl phthalate | 80 |
| Epoxidized linseed oil | 2 |
| Tricresyl phosphate | |
| Bisphenol A-diglycidylether | 3 |
| Zn laurate | 0.6 |
| Ba—12-hydroxy stearate | 1.2 |
| 1,3-Dicarbonyl compound listed in Table IV | 0.1 |

This formulation was blended and sheeted off on a two-roll mill to form sheets 1 mm thick.

The sheets were heated in air in a Geer oven at 175° C. to evaluate heat stability, and the time in minutes noted for the sheet to develop a noticeable discoloration and/or embrittlement. Initial color and color after heating at 175° C. for 30 minutes were measured for yellowness using a Hunter color difference meter.

The results obtained are given in Table IV:

TABLE IV

| Example No. | 1,3-Dicarbonyl Compound | Heat Stability (minutes) | Initial Color | Heat Color |
| --- | --- | --- | --- | --- |
| | None | 30 | 33 | — |
| Control 1 | Dibenzoylmethane | 50 | 18 | 24 |
| Control 2 | Dibenzoyl acetylmethane | 45 | 21 | 37 |
| 37 | 1,8-Bis(2-hydroxybenzoyl)octane-2,7-dione | 70 | 10 | 14 |
| 38 | 1,6-Dibenzoyl-3-hexene-2,5-dione | 75 | 9 | 13 |
| 39 | 1,3-Bis(benzoylacetyl)benzene | 80 | 9 | 12 |
| 40 | 1,7-Dibenzoyl-4-thiaheptane-2,6-dione | 75 | 8 | 13 |
| 41 | 1,9-Dibenzoyl-5-thianonane-2,8-dione | 70 | 10 | 14 |
| 42 | 1,9-Dibenzoyl-4,6-dithianonane-2,8-dione | 70 | 11 | 14 |
| 43 | 2,3-Bis(benzoylacetyl)bycyclo(2,2,1)heptene-5 | 65 | 10 | 15 |
| 44 | N,N,N—Tris(benzoylacetylethyl)amine | 65 | 11 | 15 |
| 45 | Zn[1,4-Dibenzoylbutane-2,3-dione]$_2$ | 70 | 9 | 13 |
| 46 | Zn[1,6-Dibenzoyl-3-hexene-2,5-dione]$_2$ | 70 | 10 | 12 |
| 47 | Zn[1,3-Bis(acetoacetyl)benzene]$_2$ | 75 | 9 | 14 |

These results demonstrate the remarkable effectiveness of the 1,3-di-carbonyl compounds of this invention in color protection and heat stability, compared to the control compounds.

EXAMPLES 48 TO 70

A group of polyvinyl chloride resin compositions was prepared having the following formulation:

| Ingredient | Parts by Weight |
| --- | --- |
| Polyvinyl chloride (Geon 103 EP) | 100 |
| Dioctyl phthalate | 50 |
| Stearic acid | 0.3 |
| Zn p-t-butyl benzoate | 0.5 |
| Ba—stearate | 0.7 |
| 1,12-dibenzoyl decane-2,11-dione | 0.05 |
| Epoxy compound or phosphite as shown in Table V | 1.0 |

This formulation was blended and sheeted off on a two-roll mill to form sheets 1 mm thick.

The sheets were heated in air in a Geer oven at 175° C. to evaluate heat stability, and the time in minutes noted for the sheet to develop a noticeable discoloration and/or embrittlement. Initial color and color after heating at 175° C. for 60 minutes also were measured, using a Hunter color difference meter to determine the amount of yellowness on a scale where the higher the numerical value, the more yellow the sample is.

The results obtained are given in Table V:

TABLE V

| Example No. | 1,2-Epoxide organic phosphite | Amount | Heat Stability (minutes) | Initial Color | Heat Color |
|---|---|---|---|---|---|
| Control | None and also without 1,12-dibenzoyl decane-2,11-dione | — | 40 | 33 | 56 |
| 48 | None | — | 60 | 15 | 21 |
| 49 | Epoxysoybean oil | 2.0 | 90 | 9 | 13 |
| 50 | Epoxylinseed oil | 2.0 | 95 | 8 | 12 |
| 51 | Epoxydized codliver oil | 2.0 | 85 | 11 | 14 |
| 52 | Epoxydized polybutadiene | 2.0 | 90 | 9 | 13 |
| 53 | Tris(epoxypropyl) isocyanurate | 2.0 | 80 | 10 | 14 |
| 54 | Octyl-epoxystearate | 2.0 | 85 | 9 | 12 |
| 55 | 3-(2-Xenoxy)-1,2-epoxypropane | 2.0 | 80 | 12 | 16 |
| 56 | Vinylchclohexene-diepoxide | 2.0 | 85 | 11 | 15 |
| 57 | Bisphenol a diglycidylether | 2.0 | 95 | 8 | 13 |
| 58 | 3,4-Epoxycyclohexylmethyl-3,4-epoxycyclohexane-carboxylate | 2.0 | 90 | 10 | 15 |
| 59 | Triphenylphosphite | 1.0 | 85 | 11 | 15 |
| 60 | Tris(nonylphenyl)phosphite | 1.0 | 90 | 9 | 13 |
| 61 | Tristearylphosphite | 1.0 | 80 | 12 | 16 |
| 62 | Octyl diphenylphosphite | 1.0 | 100 | 8 | 12 |
| 63 | Diphenyl isodecylphosphite | 1.0 | 100 | 8 | 11 |
| 64 | Tris(2,4-di-t-butylphenyl)phosphite | 1.0 | 90 | 10 | 13 |
| 65 | Tetra(C$_{12-15}$alkyl) bisphenol A disphosphite | 1.0 | 105 | 7 | 10 |
| 66 | Di(nonylphenyl)4,4'-isopropylidene bis(2-t-butylphenol)phosphite | 1.0 | 90 | 9 | 12 |
| 67 | Phenyl bisphenol A pentaerythritol diphosphite | 1.0 | 95 | 8 | 11 |
| 68 | Hydrogenated bisphenol A polyphosphite | 1.0 | 80 | 11 | 16 |
| 69 | Triphenyl phosphite Diphenyl acid phosphite | 0.7 0.3 | 100 | 8 | 11 |
| 70 | Diisodecylpentaerythritol diphosphite | 1.0 | 90 | 10 | 13 |

These results demonstrate the advantageous use 1,2-epoxides or organic phosphites together with 1,3-dicarbonyl compounds in accordance with this invention.

Having regard to the foregoing disclosure, the following is claimed as the patentable and inventive embodiments thereof:

1. A polyvinyl halide resin composition having improved resistance to deterioration when heated at 350° F., comprising a polyvinyl halide resin formed at least in part of the recurring group:

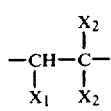

and having a halogen content in excess of 40%, where $X_1$ is halogen and $X_2$ is either hydrogen or halogen, and a 1,3-dicarbonyl compound having the formula:

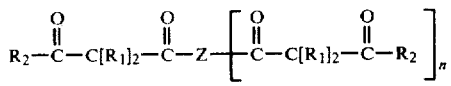

wherein:
R$_1$ is selected from the group consisting of hydrogen, hydrocarbon groups having from one to about eighteen carbon atoms and such groups substituted with one or more groups selected from the group consisting of halogen, hydroxy, alkoxy OR$_1$, ester COOR$_1$, alkyl and alkoxycarbonyl alkyl having from one to about eighteen carbon atoms, and

R$_2$ is selected from the group consisting of hydrocarbon having from one to about eighteen carbon atoms and such groups substituted with one or more groups selected from the group consisting of halogen, hydroxy, alkoxy OR$_1$, ester COOR$_1$, alkyl and alkoxycarbonyl alkyl having from one to about eighteen carbon atoms;
one R$_1$ and R$_2$ may be linked together as an alkylene group to form a cyclic or ring structure;
n is a number from 1 to 3; and
Z is a polyvalent linking radical selected from the group consisting of a direct linkage between the

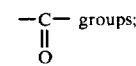

polyvalent hydrocarbon R$_3$;

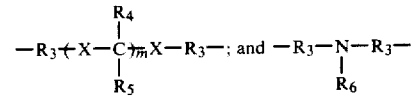

wherein:
R$_3$ is a polyvalent hydrocarbon group having from one to about eighteen carbon atoms;
R$_4$ and R$_5$ are selected from the group consisting of hydrogen and hydrocarbon groups having from one to about eighteen carbon atoms; and R$_4$ and R$_5$ may be linked together as an alkylene to form a cyclic or ring structure;
X is —O— or —S—;
m is 0 or 1; and
R$_6$ is selected from the group consisting of hydrogen, hydrocarbon having from one to about eighteen carbon atoms, and —R$_3$—; or metal and organotin enolate salts of said 1,3-dicarbonyl compounds.

2. A polyvinyl halide resin composition in accordance with claim 1 in which the polyvinyl halide resin is polyvinyl chloride homopolymer.

3. A polyvinyl halide resin composition in accordance with claim 1 in which the polyvinyl halide resin is a copolymer of vinyl chloride and a copolymerizable monomer.

4. A polyvinyl halide resin composition in accordance with claim 3 in which the copolymerizable monomer is vinyl acetate.

5. A stabilizer composition capable of enhancing the resistance to deterioration by heat and/or light of polyvinyl halide resins, comprising a 1,3-dicarbonyl compound having the formula:

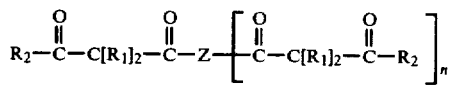

wherein:
R$_1$ is selected from the group consisting of hydrogen, hydrocarbon groups having from one to about eighteen carbon atoms and such groups substituted with one or more groups selected from the group consisting of halogen, hydroxy, alkoxy OR$_1$, ester COOR$_1$, alkyl and alkoxycarbonyl alkyl having from one to about eighteen carbon atoms, and

R$_2$ is selected from the group consisting of hydrocarbon having from one to about eighteen carbon atoms and such groups substituted with one or more groups selected from the group consisting of halogen, hydroxy, alkoxy OR$_1$, ester COOR$_1$, alkyl and alkoxycarbonyl alkyl having from one to about eighteen carbon atoms;
one R$_1$ and R$_2$ may be linked together as an alkylene group to form a cyclic or ring structure;
n is a number from 1 to 3; and
Z is a polyvalent linking radical selected from the group consisting of a direct linkage between the

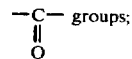

polyvalent hydrocarbon R$_3$;

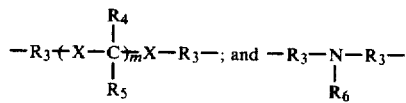

wherein:
R$_3$ is a polyvalent hydrocarbon group having from one to about eighteen carbon atoms;
R$_4$ and R$_5$ are selected from the group consisting of hydrogen and hydrocarbon groups having from one to about eighteen carbon atoms; and R$_4$ and R$_5$ may be linked together as an alkylene to form a cyclic or ring structure;
X is —O— or —S—;
m is 0 or 1; and
R$_6$ is selected from the group consisting of hydrogen, hydrocarbon having from one to about eighteen carbon atoms, and —R$_3$—; or metal and organotin enolate salts of said 1,3-dicarbonyl compounds, and an additional polyvinyl halide resin heat stabilizer.

6. A stabilizer composition according to claim 5 in which the additional heat stabilizer is selected from the group consisting of metal salts of carboxylic acids; metal salts of hydrocarbon-substituted phenols; phenolic antioxidants; 1,2-epoxides and organic phosphites.

* * * * *